United States Patent [19]

Satyamurthy et al.

[11] Patent Number: 5,510,522
[45] Date of Patent: Apr. 23, 1996

[54] SYNTHESIS OF N-FORMYL-3,4-DI-T-, BUTOXYCARBONYLOXY-6-(TRIMETHYLSTANNYL)-L-PHENYLALANINE ETHYL ESTER AND ITS REGIOSELECTIVE RADIOFLUORODESTANNYLATION TO 6-[$^{18}$F]FLUORO-L-DOPA

[75] Inventors: Nagichettiar Satyamurthy, Los Angeles; Jorge R. Barrio, Agoura Hills, both of Calif.; Allyson J. Bishop, Wahnemuhle, Germany; Mohammad Namavari, Los Angeles, Calif.; Gerald T. Bida, Shreveport, La.

[73] Assignee: Regents of the University of California, Oakland, Calif.

[21] Appl. No.: 393,428

[22] Filed: Feb. 22, 1995

Related U.S. Application Data

[63] Continuation-in-part of Ser. No. 903,915, Jun. 25, 1995, Pat. No. 5,393,908.

[51] Int. Cl.$^6$ .................................................. C07C 229/00
[52] U.S. Cl. .................................................. 562/446
[58] Field of Search .................................................. 562/446

[56] References Cited

U.S. PATENT DOCUMENTS 5,393,908  2/1995  Satyamurthy et al. .................. 556/87

Primary Examiner—Porfiro Nazario-Gonzales

[57] ABSTRACT

A process for forming a 6-fluoro derivative of compounds in the L-Dopa family comprising the steps of protecting the groups attached to the benzene ring in the compound followed by serially reacting the protected compound with (a) iodine and silver trifluoroacetic acid; (b) $Bb_3$; (c) ditbutyldicarbonate; (d) hexamethyltin; (e) a fluoro compound; (f) hydrobromic acid; and (g) raising the pH to ≦7.

3 Claims, 1 Drawing Sheet

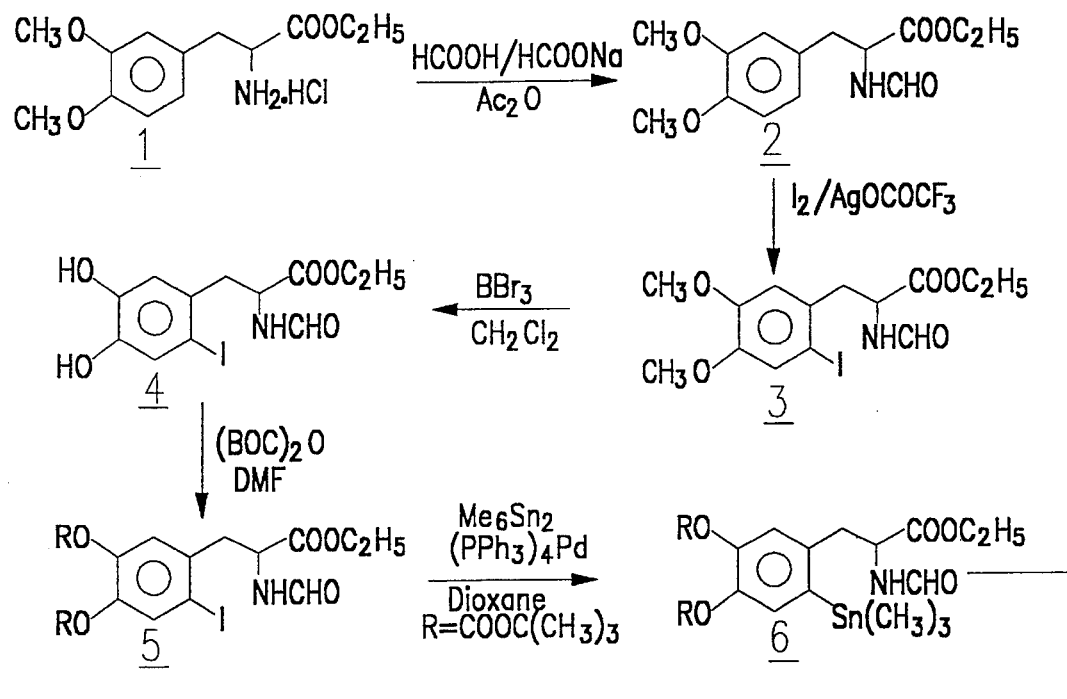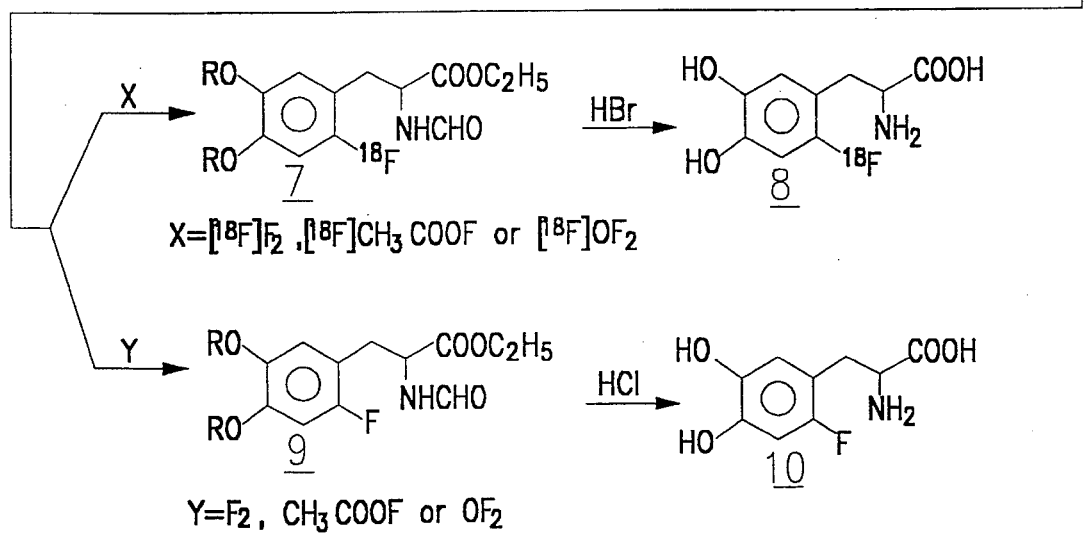

SYNTHESIS OF N-FORMYL-3,4-DI-T-BUTOXYCARBONYLOXY-6-(TRIMETHYLSTANNYL)-L-PHENYLALANINE ETHYL ESTER AND ITS REGIOSELECTIVE RADIOFLUORODESTANNYLATION TO 6-[$^{18}$F] FLUORO-1-DOPA

This invention was made in part with government support from a Department of Energy Grant DE-FC0387-ER60615, NIH Grant PO1-NS-15654 and NIMH Grant RO1-MH-37916.

This is a Continuation-In-Part of U.S. application Ser. No. 07/903,915 filed on Jun. 25, 1995, now U.S. Pat. No. 5,393,908.

BACKGROUND

The present invention relates to a high yield synthesis of a tin-containing precursor for the preparation of fluorolabeled L-dopa and a L-dopa related compounds and the process for preparing that precursor and the labeled compound. More specifically, the invention relates to new alkyltin compounds (N-formyl-3,4-di-t-butoxycarbonyloxy-6-(trimethylstannyl)-L-phenylalanine ethyl ester and related compounds), its preparation and the production of 6-[$^{18}$F] fluoro-L-dopa by reaction with three different cyclotron-produced F-18 labeled fluorinating agents ($F_2$, acetyl hypofluorite, and $OF_2$).

Several different methods have been disclosed in the literature for preparing fluorine labeled L-dopa. However, they are all time consuming, require numerous processing steps to produce pure product and result in low to modest yields.

The labeled L-dopa compound is radioactive and as a result has a limited lifetime. Also, because of the radioactivity of the material, it is desired that the handling and processing of the material be kept to a minimum and that the yield of the desired isomer be as high as possible to eliminate the need to produce several batches of the 6-isomer to meet daily laboratory needs.

Thus, there is a need for a shelf stable precursor. Further, there is a need for a high yielding process which can be performed in a short period of time.

SUMMARY

These needs are met by the present invention which comprises new alkyltin compounds (N-formyl-3,4-di-t-butoxycarbonyloxy-6-(trimethylstannyl)-L-phenylalanine ethyl ester and related compounds), its preparation, and the production of 6-[$^{18}$F]fluoro-L-dopa by reaction with three different cyclotron produced F-18 labeled fluorinating agents ($F_2$, acetyl hypofluorite, and $OF_2$).

More particularly the invention comprises the process of:

(1) forming N-formyl-3,4-dimethoxy-L-phenylalanine ethyl ester by reacting 3,4-dimethoxy-L-phenylalanine ethyl ester-hydrochloride with sodium formate, (2) reacting the product of step (1) with acyl hypoiodite to form N-formyl-3,4-dimethoxy-6-iodo-L-phenylalanine ethyl ester, (3) exposing the product of step (2) to $BBr_3$ to form N-formyl-3,4-dihydroxy-6-iodo-L-phenylalanine ethyl ester, (4) reacting the product of step (3) with di-t-butyl dicarbonate to produce N-formyl-3,4-di-t-butoxycarbonyloxy-6-iodo-L-phenylalanine ethyl ester, and (5) reacting the product of step (5) with hexamethylditin to form N-formyl-3,4-di-t-butoxycarbonyloxy-6-(trimethylstannyl)-L-phenylalanine ethyl ester.

6-[$^{18}$F]fluoro-L-dopa is prepared by bubbling [$^{18}$F]$CH_3COOF$, [$^{18}$F]$F_2$, or [$^{18}$F]$OF_2$ through the product of step 5 in organic solvent and treating the resultant product with hydrobromic acid followed by partial neutralization with NaOH and purifying by preparative HPLC.

This process can also be performed to produce labeled fluoro L-dopa related compounds.

DRAWINGS

These and other features, aspects and advantages of the present invention will become better understood with reference to the following description, appended claims, and accompanying drawing, where:

FIG. 1 is a representation of the steps performed to obtain the claimed tin compound and the fluorinated compound produced from the tin compound.

DESCRIPTION

Several neuropsychiatric diseases are believed to result from alterations in the neurotransmitter systems such as the dopaminergic system. It has therefore become beneficial to characterize the intercerebral distribution and metabolism of biological materials which naturally occur in the brain and to evaluate the result of abnormal levels of these materials. A useful technique to perform this characterization is positron emission tomography (PET) with the assistance of a labeled material which can readily cross the blood-brain barrier. Using this technique cholinergic, opiate and benzodiazepine receptors have been studied in humans and living animals.

The dopamine system is the most widely studied neurotransmitter system. Dopamine deficiencies in the nigrostriatal system is a characteristic of Parkinson's disease and deficiencies or disturbances in dopamine metabolism are believed to be responsible for Huntington's disease, schizophrenia and the effects caused by drug abuse (i.e., cocaine, amphetamines) as well as other locomotion and mood related problems. The literature shows that structural analogues of L-dopa, e.g. m-tyrosine have many pharmacological effects in common with the parent compound. Thus, o- and m-tyrosine produced sympathomimetic signs as well as central nervous excitatory actions. Like L-dopa, m-tyrosine increased motor activity of normal mice and had an awakening effect in reserpinized mice as well as a central hypotensive effect (Rubenson, A, "Analysis of the Action of m-Tyrosine on Blood Pressure in the Conscious Rat: Evidence for a Central Hypotensive Effect", *J. Pharm. Pharmac.*, 23 p. 412–419 (1971). The hypotensive effect of the structurally related amino-acid L-α-methyldopa (α-MD) was also studied by Rubenson, (Rubenson, A "Further Studies on the Mechanism of the Central Hypotensive Effect of L-Dopa, DL-m-tyrosine and L-α-methyl dopa" *J. Pharm. Pharmae,* 23 p. 228–230 (1971). Reporting on the antiparkinson effect of related compounds Ungerstedt, et al. stated that m-Tyrosine, like Dopa penetrates into the brain and is subsequently converted to m-tyrosine, an amino acid which structurally resembles DA (dopamine) formed from L-dopa, mimicking the behavioral effect of L-Dopa treatment (Ungerstedt, U, "Action of M-Tyrosine in Experimental Models: Evidence for Possible Antiparkinsonian Activity "*European Journal of Pharmacology* 21 page 230–237, (1973). A material found to be particularly useful for use in PET to characterize and diagnose abnormalities in the dopaminergic system is 6-[$^{18}$F]fluoro-L-dopa. Because of the desirable L-dopa-like characteristics of m-tyrosine, both invivo and invitro De Jesus synthesized and studied L-dopa analogs, particularly radiobrominated 6-bromo-m-tyrosine for use in PET scanning. He further suggested that radiofluorinated m-tyrosine is a suitable positron-emitting analog, the m-tyrosine decarboxzlating to m-tyrosine which acts as a false dopamine neurotransmitter. De Jesus, O. T., et al., Radiobrominated m-Tyrosine Analog as Potential CNS L-Dopa PET Tracer" *Biochemical and Biophysical Research Communications*, 150 No. 3, p. 1027–1031 (Feb. 15, 1988). Further, while m-tyrosine has effects and activity similar to L-dopa, formation of the unwanted o-methyl metabolite is avoided. Further, these compounds are suitable tracers for turnover of dopamine, the decarboxylation product of L-dopa. De Jesus, O. T. "Synthesis of Radiobrominated m-Tyrosine, *Journal of Labelled Compounds and Radiopharmaceuticals*, XXVII, No. 2, p. 189–194 (1989).

Accordingly referenced herein to L-dopa related compounds or L-dopa family shall include, but not be limited to, dopamine, L-tyrosine, m-tyrosine and L-α-methyldopa.

Both nucleophilic and electrophilic processes have been proposed for the production of labeled L-dopa. Nucleophilic synthesis requires a multi-step process with sensitive materials and is therefore difficult to perform on a routine basis. Electrophilic processes are generally preferred because they are more amenable to routine production, are more regioselective, and the resultant products are easily purified by single pass preparative HPLC. Several electrophilic methods to prepare this material have been used in the past. One method is based on the reaction of [$^{18}$F]acetyl hypofluorite with a partially blocked dopa derivative in acetic acid. The second method involves the reaction of L-dopa with [$^{18}$F]F$_2$ in liquid HF. A third method reacts [$^{18}$F]acetyl hypofluorite with a fully derivatized dopa substrate to produce 2- and 6-fluorodopa in about equal amounts. Fluorodemetallation methods involve use of dopa-silane or dopa-mercury precursors. The first two processes produce a mixture of three isomers and the third a mixture of two isomers which must be treated using time-consuming procedures to separate out the 6-isomer. Processes 1 and 2 have maximum yields of about 3%. The desilylation process produces the desired isomer in yields of only about 8% but the preparation of the silane precursor is difficult and gives very low yields. The fluoro-demercuration process can result in yields as high as 11%. The third process results in yields higher than the first two processes but lower than the desilylation process.

While the present invention comprises a multistep process, it is easy to perform, gives high yields for each step of the process and produces new, shelf-stable alkyl tin compounds (N-formyl-3,4-di-t-butoxycarbonyloxy-6-(trimethylstannyl)-L-phenylalanine ethyl ester and related materials). This material can then react rapidly with [$^{18}$F]CH$_3$COOF, [$^{18}$F]F$_2$, or [$^{18}$F]OF taken alone or in combination to give high yields of 6-[$^{18}$F]fluoro-L-dopa which can be injected into a patient and tracked by PET.

More particularly a process embodying features of the invention comprises the steps as shown in FIG. 1 of:

(1) reacting 3,4-dimethoxy-L-phenylalanine ethyl ester-hydrochloride with sodium formate to produce N-formyl-3,4-dimethoxy-L-phenylalanine ethyl ester, (2) forming N-formyl-3,4-dimethoxy-6-iodo-L-phenylalanine ethyl ester by reacting the product of step one with acyl hypoiodite, (3) mixing the product of step 2 with BBr$_3$ to form N-formyl-3,4-dihydroxy-6-iodo-L-phenylalanine ethyl ester, (4) reacting the product of step 3 with di-t-butyl dicarbonate to produce N-formyl-3,4-di-t-butoxycarbonyloxy-6-iodo-L-phenylalanine ethyl ester, and (5) reacting the product of step 4 with hexamethylditin to form N-formyl-3,4-di-t-butoxycarbonyloxy-6-(trimethylstannyl)-L-phenylalanine ethyl ester.

6-[$^{18}$F]fluoro-L-dopa is prepared by bubbling [$^{18}$F]CH$_3$COOF, [$^{18}$F]F$_2$, or [$^{18}$F]OF$_2$ through the product of step 5 and treating the resultant product with hydrobromic acid followed by partial neutralization with NaOH.

The formulation of the protected L-dopa derivative 1 by formic acid/acetic anhydride gave the N-formyl compound 2 in good yields. The iodination of product 2 by acetyl hypoiodite, generated in situ, gave exclusively the monoiodo derivative 3. While bromination has been found to be suitable in the process of adding tin to simple molecules, bromination has been found to be unacceptable in the present reaction scheme and iodine has been found to be particularly facile. The dimethoxy groups in 3 were hydrolyzed and then protected with tert-butoxycarbonyl (t-boc) groups. The t-boc protection of the catechol facilitates fluoro-destannylation and also the final hydrolysis after the fluorination step. Moreover, the t-boc groups can easily be deprotected with off-the-shelf HBr (48%) in less than 10 minutes whereas dimethoxy groups generally require HI (55%), distilled from red phosphorus under hydrogen, which is then stabilized with hypophophorus acid and stored in sealed ampules in the dark at low temperatures. An alternate to t-boc is acetoxy, alkoxy compounds or equivalent O-protecting groups.

Reaction of the iodo derivative 5 with hexamethylditin gave the ipso substituted tin precursor 6 as a room temperature shelf-stable and crystalline white solid in good yields.

The fluorodestannylation of 6, unlike other fluorodemetallation reactions proceeded at an unexpectedly rapid rate and give unexpected high yields. Compound 6 reacts with equal ease with the traditional electrophilic fluorinating agents such as fluorine and acetyl hypofluorite as well as the recently rediscovered oxygen difluoride. For instance, both F$_2$ and OF$_2$ smoothly react with the tin precursor 6 to give the fluoro derivative 9 in isolated yields >65%.

The tin precursor 6 was also reacted with $^{18}$F-labeled acetyl hypofluorite, fluorine and oxygen difluoride. The $^{18}$F-fluoro intermediate 7 was readily hydrolyzed by HBr (48%) and the product purified by preparative HPLC. The overall radiochemical yields obtained with [$^{18}$F]F$_2$ and [$^{18}$F]OF$_2$ by the present method are the highest heretofore achieved for the synthesis of 6-[$^{18}$F]fluorodopa. Since more than a curie of [$^{18}$F]F$_2$ and [$^{18}$F]OF$_2$ mixture can easily be produced via $^{18}$O (p,n) $^{18}$F reaction (Bida, G. T., Hendry, G. O., Bishop, A. J. and Satyamurthy, N. (1991) [F-18]F$_2$ Production via low energy proton irradiation of [0–18]O$_2$ plus F$_2$. Proceedings of the Fourth International Workshop on Targetry and Target Chemistry, Villigen PSI, Switzerland, 9–12 Sep. 1991; Bishop, A. J., Satyamurthy, N., Bida, G., Phelps, M. E. and Barrio, J. R. (1991) Spectroscopic identification and chemical reactivity of the electrophilic F-18 species generated in the 0–18/F-18 gas target system. *J. Nucl. Med.* 32, 1010), a routine and large scale production (>100 mCi) of 6-[$^{18}$F]fluorodopa ready for injection is now feasible.

The Examples below set forth methods incorporating the invention for preparing the tin precursor and the labeled L-dopa compound.

EXAMPLE 1

Preparation of the Tin Precursor

1. N-Formyl-3,4-dimethoxy-L-phenylalanine ethyl ester 2

To a mixture of 3,4-dimethoxy-L-phenylalanine ethyl ester-hydrochloride 1 (Luxen, A., Perlmutter M., Bida, G. T., Van Moffaert, G., Cook, J. S., Satyamurthy, N., Phelps, M. E. and Barrio, J. R. (1990) Remote, semiautomated production of 6-[$^{18}$F]fluoro-L-dopa for human studies with PET. *Appl. Radiat. Isot.* 41, 275) (5.3 g, 18.3 mmol) and sodium formate (1.44 g, 21.2 mmol) in formic acid (52 mL) cooled in an ice bath was added acetic anhydride (20 mL) and stirred at room temperature for 3 h. After addition of ethanol (40 mL) the mixture was stirred at room temperature for an additional 3 h and evaporated. The residue was dissolved in ethyl acetate, filtered and the insoluble material was washed with, ethyl acetate. The combined filtrates were washed successively with aqueous 10% HCl, saturated aqueous NaHCO$_3$ and saturated aqueous NaCl. The organic extract was dried over anhydrous MgSO$_4$ and concentrated under reduced pressure to a yellow syrup. Crystallization of the syrup from ethyl acetate-petroleum ether give a white solid 2 (3.1 g, 61%); m.p. 102°–103° C.

2. N-Formyl-3,4-dimethoxy-6-iodo-L-phenylalanine ethyl ester 3

Iodine (2.1 g, 8.3 mmol) was added to a solution of dimethoxy derivative 2 (2.1 g, 7.5 mmol) and silver trifluoroacetate (2.0 g, 9.1 mmol) in methylene chloride (110 mL) and the reaction mixture was stirred at room temperature for 48 h. The yellow precipitate that formed was filtered and washed with methylene chloride. The combined filtrates were washed with 1M Na$_2$S$_2$O$_5$ (2×75 mL), water (2×75 mL), dried and concentrated under reduced pressure to give a solid residue. Recrystallization of this residue from ethyl acetate and petroleum ether gave a white solid 3 (2.3 g, 75%); m.p. 151°–152° C.

3. N-Formyl-3,4-dihydroxy-6-iodo-L-phenylalanine ethyl ester 4

To a solution of iodo derivative 3 (2 g, 4.9 mmol) in methylene chloride (35 mL) cooled in a −78° C. bath was added BBr$_3$ (17.5 mL of 1M solution in methylene chloride) and the mixture was stirred at −78° C. for 15 min. The cooling bath was removed and the stirring continued until the mixture reached ambient temperature (~30 min). Finally, the reaction mixture was poured into ice water (100 mL), stirred at room temperature for 30 min. and the methylene chloride layer was separated. Evaporation of methylene chloride under reduced pressure resulted in a pale yellow solid 4 (1.2 g, 65%) m.p. 131°–132° C.

4. N-Formyl-3,4-di-t-butoxycarbonyloxy-6-iodo-L-phenylalanine ethyl ester 5

A solution of di-t-butyl dicarbonate (1.41 g, 6.47 mmol) in anhydrous DMF (10 mL) was added dropwise to a solution of iodo derivative 4 (0.82 g, 2.16 mmol) in anhydrous DMF (10 mL) and triethylamine (0.36 mL, 2.59 mmol). After stirring the reaction mixture at room temperature for 16 h, ethyl acetate (75 mL) was added and the reaction mixture was washed, with saturated aqueous NaCl solution (3×50 mL) and water (3×50 mL). Evaporation of the organic phase after drying with anhydrous Na$_2$SO$_4$ gave a yellow syrup which was chromatographed over silica gel (ethyl acetate-petroleum ether, 1:1) give a colorless oil 5 (1.02 g, 81%).

5. N-Formyl-3,4-di-t-butoxycarbonyloxy-6-(trimethylstannyl)-L-phenylalanine ethyl ester 6

Hexamethylditin (0.43 g, 1.31 mmol) was added to a mixture of iodo derivative 5 (0.51 g, 0.88 mmol) and tetrakis-triphenylphosphine palladium (0) (0.05 g) in anhydrous 1,4-dioxane (12 mL) and the reaction mixture was stirred under reflux in a nitrogen atmosphere for 6.5 h. After cooling, the black reaction mixture was filtered and the insoluble material was washed with ethyl acetate. Evaporation of the combined filtrate gave a yellow oil which was chromatographed on silica gel (ether) to give a white solid 6 (0.35 g, 65%); m.p. 49°–50°.

EXAMPLE 2

Preparation of Unlabeled L-dopa

1. N-Formyl-3,4-di-t-butoxycarbonyloxy-6-fluoro-L-phenylalanine ethyl ester 9

The electrophilic fluorinating agent, CH$_3$COOF (prepared from 200 μmol) of F$_2$ in 1% He, (Bida, G. T., Satyamurthy, N. and Barrio, J. R. (1984) The synthesis of 2-[$^{18}$F]fluoro-2-deoxy-D-glucose using glycals: A reexamination. *J. Nucl. Med.* 25, 1327) F$_2$ (1% in He, 200 μmol) or OF$_2$ (1% in He, 200 μmol), was bubbled into a solution of trimethyltin derivative 6 (0.123 g, 200 μmol) in Freon-11 (CFCl$_3$) (20 mL) at room temperature over a period of 30 min. The reaction mixture was diluted with methylene chloride (25 mL) and the organic phase was washed with 1M Na$_2$S$_2$O$_5$ (2×20 mL), water (2×20 mL) and dried (MgSO$_4$). Evaporation of solvents gave a yellow syrup which was chromatographed (silica gel, diethyl ether) to yield a colorless viscous oil 9 (41 mg, 43% in the case of CH$_3$COOF), (65 mg, 69% for F$_2$), 7(62 mg, 66% for OF$_2$).

2. 6-Fluoro-3,4-dihydroxy-L-phenylalanine (6-Fluoro-L-dopa) 10

N-Formyl-3,4-di-t-butoxycarbonyloxy-6-fluoro-L-phenylalanine ethyl ester 9 (20mg) was treated with 6.0N HCl (10 mL) and heated under reflux for 5 h. Evaporation of HCl under vacuum gave 10 the hydrochloride as a yellow solid (10 mg, 94%).

EXAMPLE 3

Preparation of [$^{18}$F] Labeled L-dopa

6-[$^{18}$F]Fluoro-3,4-dihydroxy-L-phenylalanine 8

Radiolabeled [$^{18}$F]F$_2$ was produced via $^{20}$Ne (d,α) $^{18}$F reaction in an aluminum target body (Bida, et al., Ibid.). [$^{18}$F]Acetyl hypofluorite was generated in the gas phase as reported in the literature (Bida, et al., Ibid.). Using $^{18}$O(p, n) $^{18}$F nuclear reaction, [$^{18}$F]F$_2$ [$^{18}$F]oxygen difluoride mixture was produced in an aluminum target (Bishop, et al., Ibid.; Bida, et al., Ibid.).

The preparation of 6-[$^{18}$F]fluoro-L-dopa was carried out in a system similar to that previously described for the remote, semiautomated production of 6-[$^{18}$F]]fluoro-L-dopa (Luxen, et al,, Ibid.). The electrophilic radiofluorinating agent, [$^{18}$F] CH$_3$COOF prepared from 100 μmol [$^{18}$F]F$_2$, [$^{18}$F]F$_2$ (100 μmol) or [$^{18}$F]OF$_2$ (100 μmol) was bubbled into a solution of trimethyltin derivative 6 (61 mg, 101 μmol) in Freon-11 (CFCl$_3$; 10 mL) at room temperature over a period of 10 min. The solvent was evaporated at 50° C. with a gentle stream of nitrogen and the residue dissolved in methylene chloride (10 mL) and transferred to a chromatography column (0.7 cm i.d.) packed with Na$_2$S$_2$O$_3$ (2.5 cm) and silica gel (9.5 cm) that had been equilibrated with ether. The column was eluted initially with 5 mL of ether and this portion of the ether solution was discarded. The radiolabeled intermediate 7 was then eluted with 25 mL of ether. The solvent was evaporated by bubbling nitrogen at 70° C. and the residue hydrolyzed with 48% HBr (2 mL) at 130° C. for 10 min. After cooling to room temperature, the reaction mixture was partially neutralized with 3N NaOH (1.7 mL), diluted with 1.3 mL of HPLC mobile phase (see below) and filtered (0.22 μm). The solution was injected onto an Alltech Adsorbosphere C-18 (7 μm) semiprep HPLC column (10× 300 mm; solvent: 5 mM sodium acetate, 1 mM EDTA, 0.1% HOAc, 0.01% ascorbic acid; pH: 4; flow rate, 7 mL/min). The fraction containing 6-[$^{18}$F]fluoro-L-dopa 8, as monitored by a radioactivity detector, was collected from the HPLC column, made isotonic with sodium chloride and passed through a 0.22 μm membrane filter into a sterile multidose vial. By analytical HPLC analysis (Waters μBondaPak C-18, 0.46×30 cm column; eluent: 0.1% HOAc containing 3% methanol; flow rate, 1 mL/min) the product, isolated by the semi-preparative HPLC, was found to be >99% chemically (uv 282 nm) and radiochemically pure. The enantiomeric purity of product 8 was confirmed by means of chiral HPLC (Chiral Pro=Si 100 Polyol (Serva) 4.6×250 mm; eluent: 50 mM KH$_2$PO$_4$, 1 mM CuSO$_4$; pH=4; flow rate, 1 mL/min) and found to be greater than 99% L-isomer, which suggests that no racemization occurs during the synthesis process. The final product after decay of $^{18}$F-isotope was analyzed by inductively coupled plasma spectrometry for organic and ionic tin contamination and found to be <15 ppb total (detection limit: 7 ppb). The overall synthesis took 60 min. for completion and the isolated radiochemical yields are given in Table 1. After the complete decay of $^{18}$F (~24 h), the product was also analyzed by $^1$H and $^{19}$F NMR and the data were in agreement with those of the cold preparation as given above.

TABLE 1

Radiochemical yields for the production of 6-[$^{18}$F]fluoro-L-dopa from the aryltin precursor 6.

| [$^{18}$F]Radiofluorinating agent | Radiochemical yield* (%) |
|---|---|
| CH$_3$COOF | 8 |
| OF$_2$ (+F$_2$) | 18 |
| F$_2$ | 23 |

*Theoretical maximum yield in all these reactions is 50%.

The process of the invention sets forth a reliable and high yielding procedure for preparing a new shelf-stable aryltin compound which is suitable for reacting with labeled fluorine or fluorine compounds to produce high yields (in excess of 20 percent) of very pure radiolabeled 6-fluoro-L-dopa. The process of the invention also allows the direct use of radiolabeled fluorinating agents such as [$^{18}$F]F$_2$ and [$^{18}$F]OF$_2$; and the efficient reactivity of the aryltin derivative 6 with various cyclotron-produced radiofluorinating agents which is easily accessible from a variety of nuclear reactions. The reproducible and high radiochemical yields permit a large scale production of 6-[$^{18}$F]fluorodopa with excellent chemical, radiochemical and enantiometric purities useful for multiple PET studies.

The present invention has been described in considerable detail with reference to a certain preferred version and use thereof. However, other versions and uses are possible. One skilled in the art will recognize that, along with appropriate changes in the process, the chemicals referred to above can be replaced by other chemicals in the same family. For example, the electron withdrawing group on the 3 and 4 position on the ring can be replaced by other electron with-drawing groups or, combinations of groups, such as methoxy, acetoxy or high molecular weight groups, the limiting factor being that the appended groups must be reducible to —OH in the final step of the process (methoxy is less effective than acetoxy or butoxy). Ethyl can be replaced by other alkyl groups such as methyl, butyl, or propyl; subject to limitations set forth above, one halogen can be replaced by other halogens; formyl can be replaced by other acyl groups such as acetyl; and the alkyl group in hexamethylditin can be replaced by other alkyl groups or combination of alkyl groups such as hexaethyltin. Further, fluorinated analogs of L-dopa, such as dopamine, tyrosine (L-or m-tyrosine) or L-α-methyldopa, the structure of which are shown below, can be prepared using the same techniques and the fluorinated compounds so produced can be used in the same manner as the fluorinated L-Dopa in the applications discussed above.

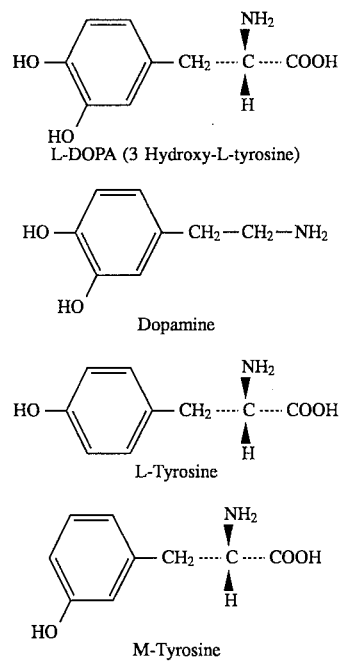

Therefore, the spirit and scope of the appended claims should not be limited to the description of the preferred versions contained herein.

What is claimed is:

1. The process of forming 6-fluoro derivatives of a benzene containing chemical compound selected from the group consisting of L-DOPA and chemicals in the L-DOPA family comprising the steps of:

(a) in the presence of acetic anhydride, reacting the chemical compound containing a benzene ring with a second chemical compound capable of protecting a chemical moiety on the first benzene carbon, (b) reacting the product of step (a) with iodine and silver trifluoroacetate, (c) reacting the product of step (b) with $BBr_3$, (d) reacting the product of step (c) with di t-butyl dicarbonate, (e) reacting the product of step (d) with hexamethyliditin;

(f) bubbling an unlabelled or radiolabeled fluorine compound selected from the group consisting of [$^{18}$F]$CH_3COOF$, [$^{18}$F]$F_2$, and [$^{18}$F]$OF_2$ and combinations thereof through the product of step (e);

(g) treating the product of step (f) above with hydrobromic acid;

(h) raising the pH of the product of step (g) above to a value $\leq 7$ by the addition of NaOH.

2. The process of claim 1 wherein the benzene containing chemical compound is selected from the group consisting of L-DOPA, dopamine, tyrosine and derivatives of L-DOPA, dopamine, and tyrosine.

3. The process of claim 2 is wherein the product of step (h) is selected from the group consisting of F-labeled L-DOPA, F-labeled dopamine and F-labeled tyrosine.

* * * * *